(12) United States Patent
Givand et al.

(10) Patent No.: US 11,141,539 B2
(45) Date of Patent: Oct. 12, 2021

(54) METERING INJECTOR FOR DELIVERING LIQUID, AND METHOD OF USING SAME

(71) Applicants: Merck Sharp & Dohme Corp., Rahway, NJ (US); Jeffrey C. Givand, North Wales, PA (US); Peter A. Basile, Bloomsbury, NJ (US)

(72) Inventors: Jeffrey C. Givand, North Wales, PA (US); Peter A. Basile, Bloomsbury, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 327 days.

(21) Appl. No.: 15/777,244

(22) PCT Filed: Dec. 14, 2016

(86) PCT No.: PCT/US2016/066437
§ 371 (c)(1),
(2) Date: May 18, 2018

(87) PCT Pub. No.: WO2017/106221
PCT Pub. Date: Jun. 22, 2017

(65) Prior Publication Data
US 2018/0326157 A1 Nov. 15, 2018

Related U.S. Application Data

(60) Provisional application No. 62/269,164, filed on Dec. 18, 2015.

(51) Int. Cl.
*A61M 5/315* (2006.01)

(52) U.S. Cl.
CPC ...... *A61M 5/3156* (2013.01); *A61M 5/31551* (2013.01); *A61M 5/3158* (2013.01);
(Continued)

(58) Field of Classification Search
CPC ............ A61M 5/3156; A61M 5/31551; A61M 5/31555; A61M 5/3158; A61M 5/31585; A61M 5/31593
See application file for complete search history.

(56) References Cited

U.S. PATENT DOCUMENTS

2003/0158523 A1    8/2003    Hjertman et al.
2012/0283653 A1    11/2012    MacDonald et al.
(Continued)

FOREIGN PATENT DOCUMENTS

EP    0611035 A1    8/1994
EP    1185322 B1    12/2005
(Continued)

OTHER PUBLICATIONS

International Search Report for PCT/US2016/066437 dated May 22, 2017, 12 pages.

*Primary Examiner* — Nathan R Price
*Assistant Examiner* — Tania Ismail
(74) *Attorney, Agent, or Firm* — Baerbel R. Brown; Catherine D. Fitch

(57) ABSTRACT

An injector for delivering liquid can include a body having a proximal end, a distal end, a longitudinal axis, and a track follower adjacent to the proximal end. A plunger can be disposed at least partially within the body and movable with respect to the body along the longitudinal axis. An actuator can be positioned at the proximal end of the body and operably connected to the plunger. The actuator can include a track having a first portion and a second portion. The first portion can limit travel of the actuator along the longitudinal axis to deliver a first predetermined amount of the liquid. The second portion can limit travel of the actuator along the longitudinal axis to deliver a second predetermined amount of the liquid. The actuator can be positionable to selectively (Continued)

control displacement of the plunger pursuant to the first portion or the second portion of the track.

18 Claims, 8 Drawing Sheets

(52) U.S. Cl.
CPC ..... *A61M 5/31553* (2013.01); *A61M 5/31555* (2013.01); *A61M 5/31585* (2013.01); *A61M 5/31593* (2013.01)

(56) References Cited

U.S. PATENT DOCUMENTS

| | | |
|---|---|---|
| 2013/0110054 A1 | 5/2013 | Raab et al. |
| 2013/0184652 A1 | 7/2013 | Smith et al. |
| 2014/0221936 A1 | 8/2014 | Edhouse et al. |

FOREIGN PATENT DOCUMENTS

| | | | | |
|---|---|---|---|---|
| WO | WO-2012125133 A1 | * | 9/2012 | .......... A61M 5/3158 |
| WO | WO2017106221 A1 | | 6/2017 | |

* cited by examiner

METERING INJECTOR FOR DELIVERING LIQUID, AND METHOD OF USING SAME

CROSS-REFERENCE TO RELATED APPLICATIONS

This application is a U.S. National Phase application under 35 U.S.C. § 371 of PCT Application PCT/US16/066437, filed Dec. 14, 2016, which claims priority from and the benefit of U.S. Provisional Application Ser. No. 62/269,164, filed Dec. 18, 2015.

BACKGROUND OF THE INVENTION

Use of a pen injector for subcutaneous delivery of a liquid or medicament to a patient is known. Conventional pen injectors are made in single-dose setting or multiple-dose setting form.

Both fixed-dose setting and variable-dose setting injectors can be multi-use, thereby allowing a health care professional or a patient to provide multiple injections with the same device. Fixed-dose setting injectors, which are sometimes referred to as "push/pull" injectors, are beneficial in their simplicity. Variable-dose setting injectors may include some form of a mechanism to allow for the selection of the different dosages.

Prior art products that provide for dose titration and delivery by subcutaneous injection include dialable dose pen injectors (e.g., products sold under the name VICTOZA™). Such products, which use a threaded engagement between an actuator and a plunger to allow continuously variable dosages to be set, may require that the user or administrator turn a dose knob on the pen until the desired dose is aligned with a dose selection line. This functionality requires the user to carefully line up the printed dose number on the dose scale with the dose selection line. Additionally, the user must actively "set the dose" for every injection, which provides an opportunity for user error on each injection completed due to imprecise setting.

Other prior art products that provide dose titration and delivery by subcutaneous injection include fixed-dosage setting pen injectors (e.g., products sold under the names BYETTA™ and LYXUMIA™). The user may be prescribed two or more different versions of the same pen injector, where the labeling describes the dosage that will be delivered by each pen version. In this format, the user must return to the pharmacy when their physician/nurse directs them to make a dosage change to a dosage they don't already have. Alternatively, the user may be provided initially with multiple pens of varying dosage strengths. The user must appropriately store the pens of dosage strengths not currently being administered until the time they are needed, and select the appropriate dosage at the time of injection. Such steps can require extra work and add complexity. Additionally, product or medicine may be wasted in certain situations.

It would be desirable to provide the simplicity of a fixed-dose setting injector to an injector that is capable or configured to provide two or more alternative dosages. The prior art does not provide such functionality, which would be beneficial to eliminate the need for patients to manage continuously variable dosage settings or multiple devices while they titrate up or down on their dosing for the product. Such functionality would also provide a simple operation sequence for the user to select and administer the desired dosage with minimal opportunity for mis-dosing, and/or eliminate potential complexities in prescription writing by physicians for multiple dose strengths of the same product in similar devices for a product where dose titration may be required. The present invention overcomes the above-identified disadvantages of the prior art, and accomplishes the above and other objectives.

SUMMARY OF THE INVENTION

In one embodiment, the present disclosure provides a multiple dose setting fixed dose pen that includes a push/pull single-dose setting fixed dose pen as the basic mechanism for metering drug as a function of the axial stroke of the dose knob or actuator. Since the delivered dose is determined by the axial stroke of the dose knob or actuator, a dose knob which can rotate into alternate or even multiple positions, thereby changing the stroke of the knob, can change the volume of drug delivered.

In another embodiment, the present disclosure is directed to an injector for delivering liquid. The injector can include a body having a proximal end, an opposing distal end, a longitudinal axis extending therebetween, and a track follower adjacent to the proximal end. A plunger can be disposed at least partially within the body and movable with respect to the body along the longitudinal axis. An actuator can be positioned at the proximal end of the body and operably connected to the plunger. The actuator can include a track having a first portion and a second portion. The first portion can limit travel of the actuator along the longitudinal axis to deliver a first predetermined amount of the liquid. The second portion can limit travel of the actuator along the longitudinal axis to deliver a second predetermined amount of the liquid. The actuator can be positionable to selectively control displacement of the plunger pursuant to the first portion or the second portion of the track.

In another embodiment, the present disclosure is directed to an injector for delivering liquid, the injector comprising: a body having a proximal end, an opposing distal end, a longitudinal axis extending therebetween, and a track follower adjacent to the proximal end. A plunger can be disposed at least partially within the body and movable with respect to the body along the longitudinal axis. An actuator can be positioned at the proximal end of the body and operably connected to the plunger. The actuator can include a track including a first portion, a second portion, and a third portion, the first portion being spaced-apart from the second portion, the first portion extending at least substantially parallel to the second portion and the longitudinal axis, the third portion extending at least substantially perpendicularly to the first portion. The first portion can limit travel of the actuator along the longitudinal axis to deliver a first predetermined amount of the liquid. The second portion can limit travel of the actuator along the longitudinal axis to deliver a second predetermined amount of the liquid, the first predetermined amount being different than the second predetermined amount. The actuator can be positionable to selectively control displacement of the plunger pursuant to the first portion or the second portion of the track. The actuator can be rotatable in a first direction to align the track follower with the first portion of the track and rotatable in a second direction to align the track follower with the second portion of the track, the first direction being opposite to the second direction.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown. In the drawings.

DETAILED DESCRIPTION OF THE INVENTION

Figure 1:
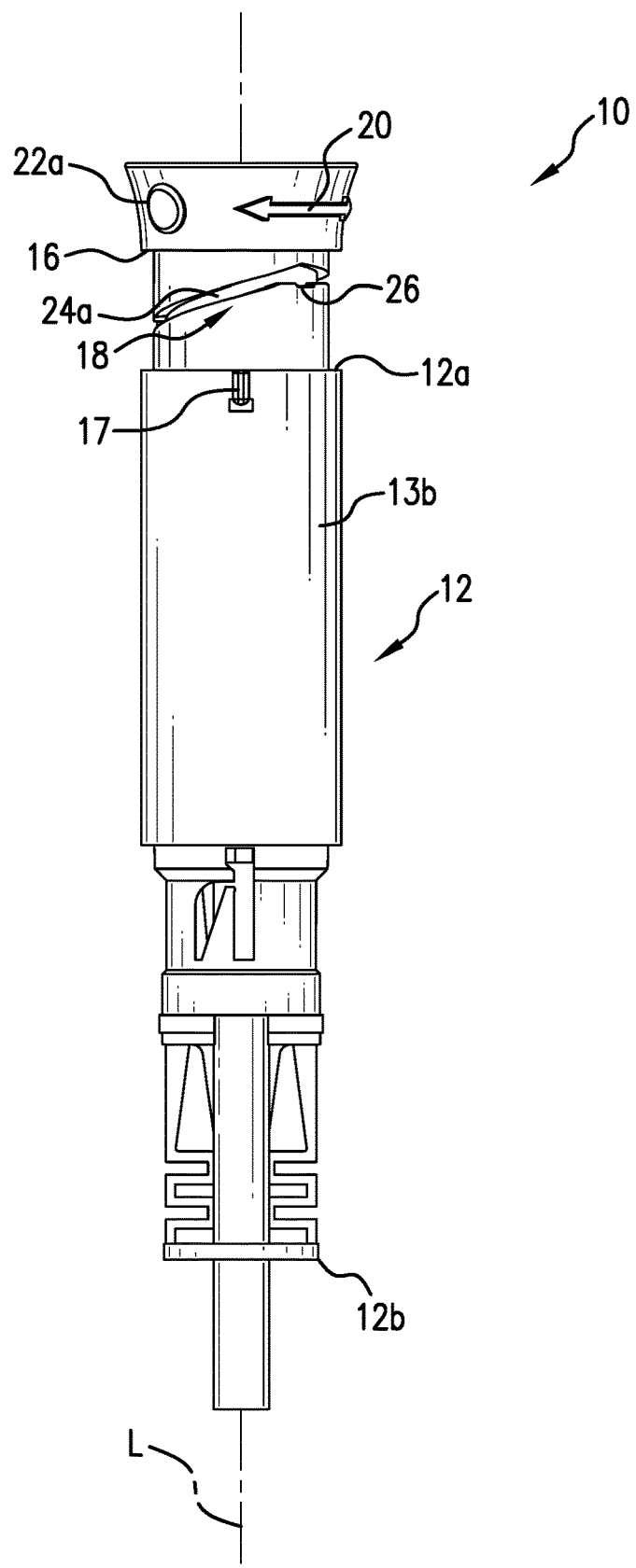
FIG. 1 is a side elevation view of an injector according to an embodiment of the present disclosure.
Figure 2:
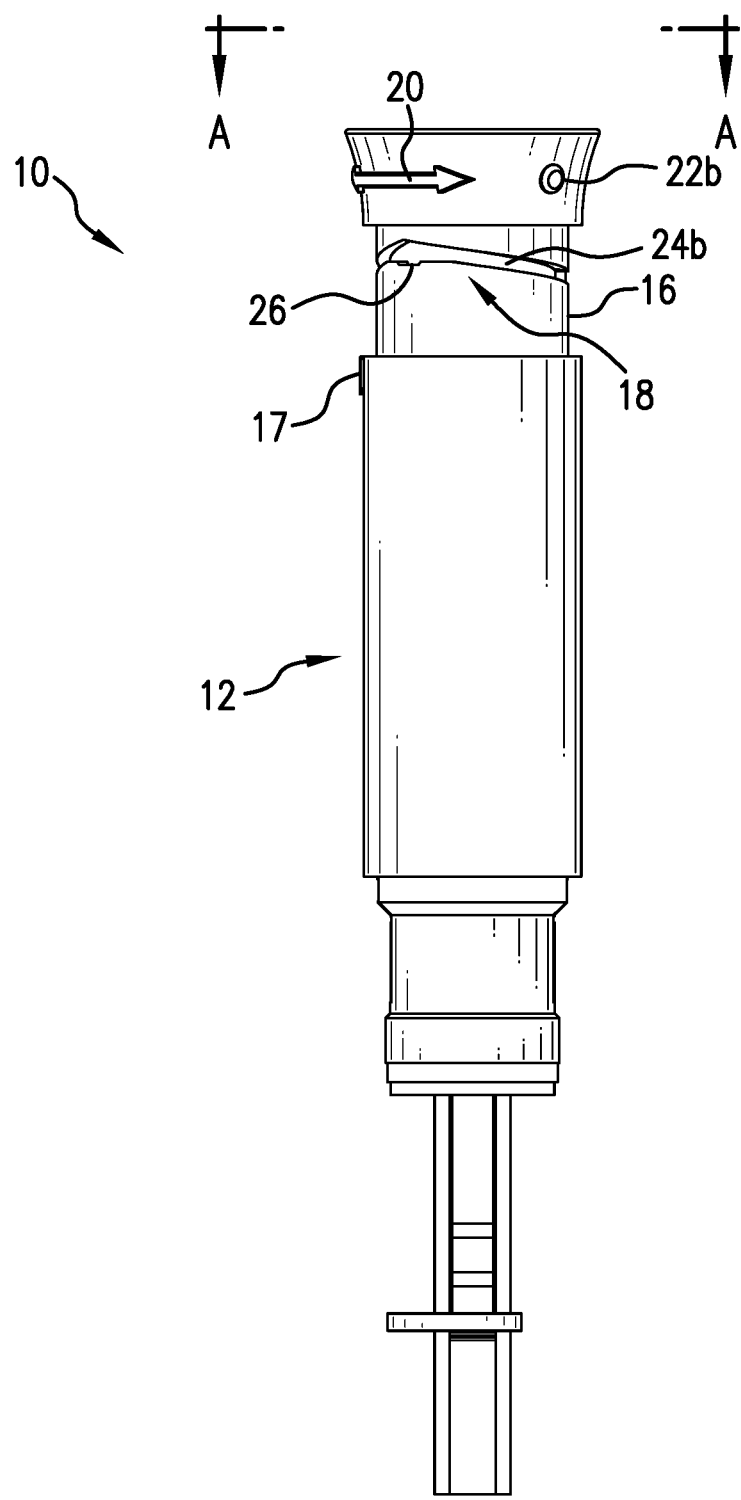
FIG. 2 is another side elevation view of the injector shown in FIG. 1.

Certain terminology is used in the following description for convenience only and is not limiting. The words "proximal," "distal," "down" and "inward" designate directions in the drawings to which reference is made. Unless specifically set forth herein, the terms "a," "an" and "the" are not limited to one element but instead should be read as meaning "at least one." The terminology includes the words noted above, derivatives thereof and words of similar import.

Referring to the drawings in detail, wherein like numerals indicate like elements throughout, FIGS. 1-7 illustrate an injector, generally designated 10, for delivering liquid, such as a medicament or a drug, to a patient. The injector 10 can be configured to deliver liquid to or within the subcutaneous layer of the skin of the patient in different dosage volumes through a simple push-pull injection mechanism. However, the injector 10 is not limited to the functionality described above. For example, the injector 10 can be used to deliver liquid or medicament to muscles, veins, arteries, bone and the like, for products such as fertility treatment, human grown hormone, insulins and/or other anti-diabetic agents. One or more of the components of the injector 10 described hereinafter may be omitted depending upon the type of needle used. Such omission is for the sake of brevity only and, therefore, is not limiting.

As described below, commercially available disposable pen injector needles and/or liquid cartridges can be used with or attached to the injector 10 to support effective usage of the injector 10. A cartridge can include a cylindrical body, possibly formed of glass, surrounding or containing the pre-filled liquid. A proximal end of the cartridge can include a piston, possibly formed of rubber, and a distal end of the cartridge can include a closure or stop. The piston and stop can enclose the liquid within the body. The stop can be designed to be pierced by the injection needle, or otherwise flowably connected to an injection needle, and the piston can be used to force liquid out of the body and through the needle. Such cartridges are known in the industry and are commercially available from Becton, Dickinson and Company of Franklin Lakes, N.J. and other suppliers to the pharmaceutical industry.

In operation, in one embodiment, the user can initially set a desired dosage (or a dosing volume) of the injector 10. A visual indicator 17 (described in detail below) can be incorporated into the design of the injector 10 to provide feedback to the user (e.g., the patient) or highlight the selected dose. The user can then attach a compatible needle to the injector 10. The user can then pull a dose knob or actuator 16 rear-ward until confirmation is obtained that the injector 10 is set to inject. At this point, the user can insert the needle attached to the injector 10 into the desired injection site of the patient, and then depress the actuator 16 inward until confirmation is obtained that the full dose is delivered to the patient, such as by the movement of the actuator 16 being impeded by a mechanical stop.

One benefit of the injector 10 of the present disclosure is that the user can select the desired dose setting when directed to do so, for example by their healthcare professional (i.e., a physician or nurse), without the need to procure a separate pen. Additionally, in one embodiment, the injector 10 eliminates or at least reduces product waste by allowing continued use of the same product in the same injector 10 by merely adjusting the dosage setting and, thereby, the injection volume.

The injector 10 can include a body 12 having a proximal end 12a, an opposing distal end 12b, and a longitudinal axis L extending therebetween (see FIG. 1). The body 12 can have a cylindrical shape, and the proximal end 12a can be open (see FIG. 4). The body 12 can include interior surface 13a and an opposing exterior surface 13b. The body 12 can have a generally cylindrical shape.

A cam follower or track follower 15 can be positioned at or adjacent to the proximal end 12a of the body 12. In one embodiment, the track follower 15 can be in the form of a projection that extends at least slightly inwardly from the interior surface 13a of the body 12 (see FIG. 4). The track follower 15 can be molded into the body 12, for example.

The visual indicator 17 can form part of or be associated with the track follower 15. The visual indicator 17 can be located on the exterior surface 13b of the body 12. For example, the visual indicator 17 can be a projection extending outwardly from the exterior surface 13b of the body 12. The visual indicator 17 can be aligned with the track follower 15 on the opposing surface of the body 12. However, the visual indicator 17 is not limited to the size, shape, placement and/or configuration shown and described herein. For example, the visual indicator 17 can be indicia on the exterior surface 13b of the body 12 or can be a groove extending at least slightly inwardly into the exterior surface 13b of the body 12. Alternatively, the visual indicator 17 can be a transparent or partially transparent window that permits the track follower 15 to be visible. Furthermore, the visual indicator 17 can be located on or incorporated into any other component of the injector 10 described below.

Figure 3:
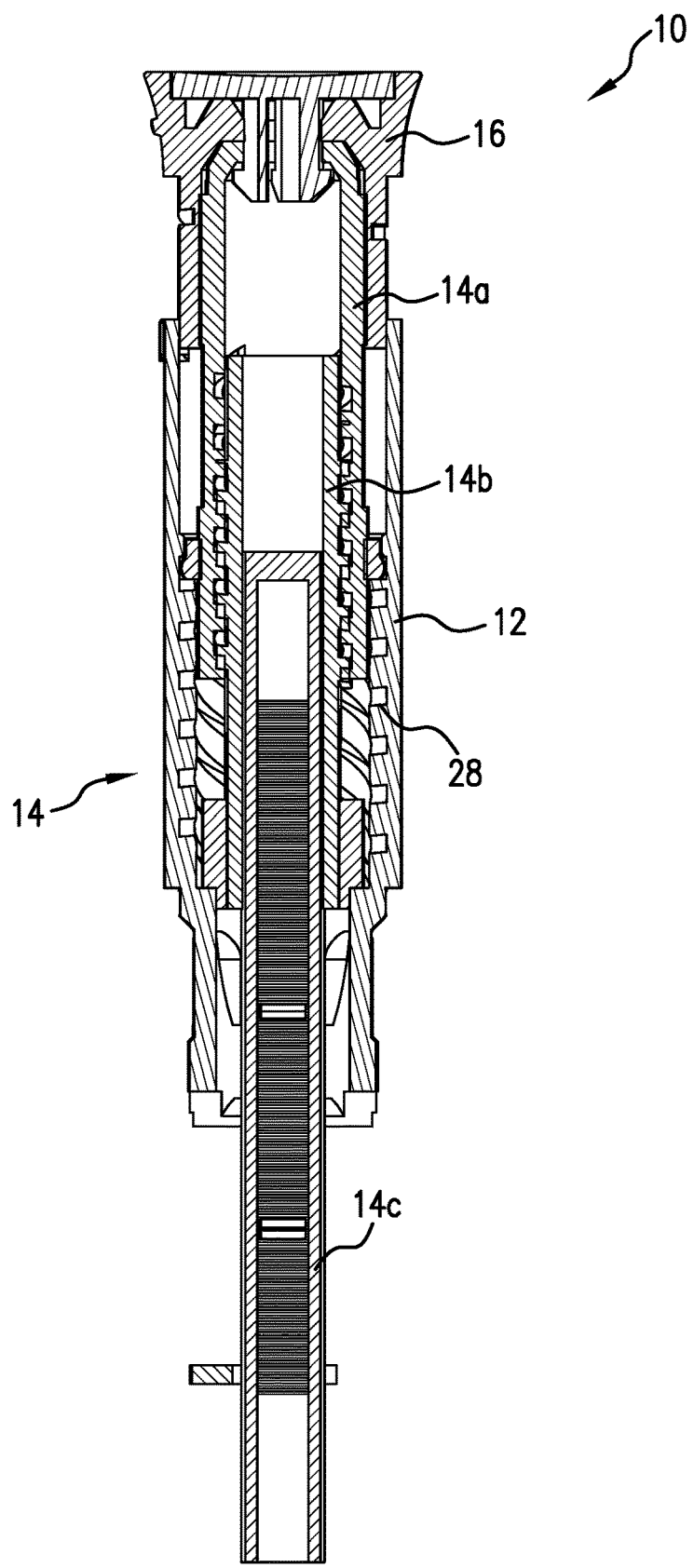
FIG. 3 is a cross-sectional elevation view of the injector taken along line A-A of FIG. 2.
Figure 4:
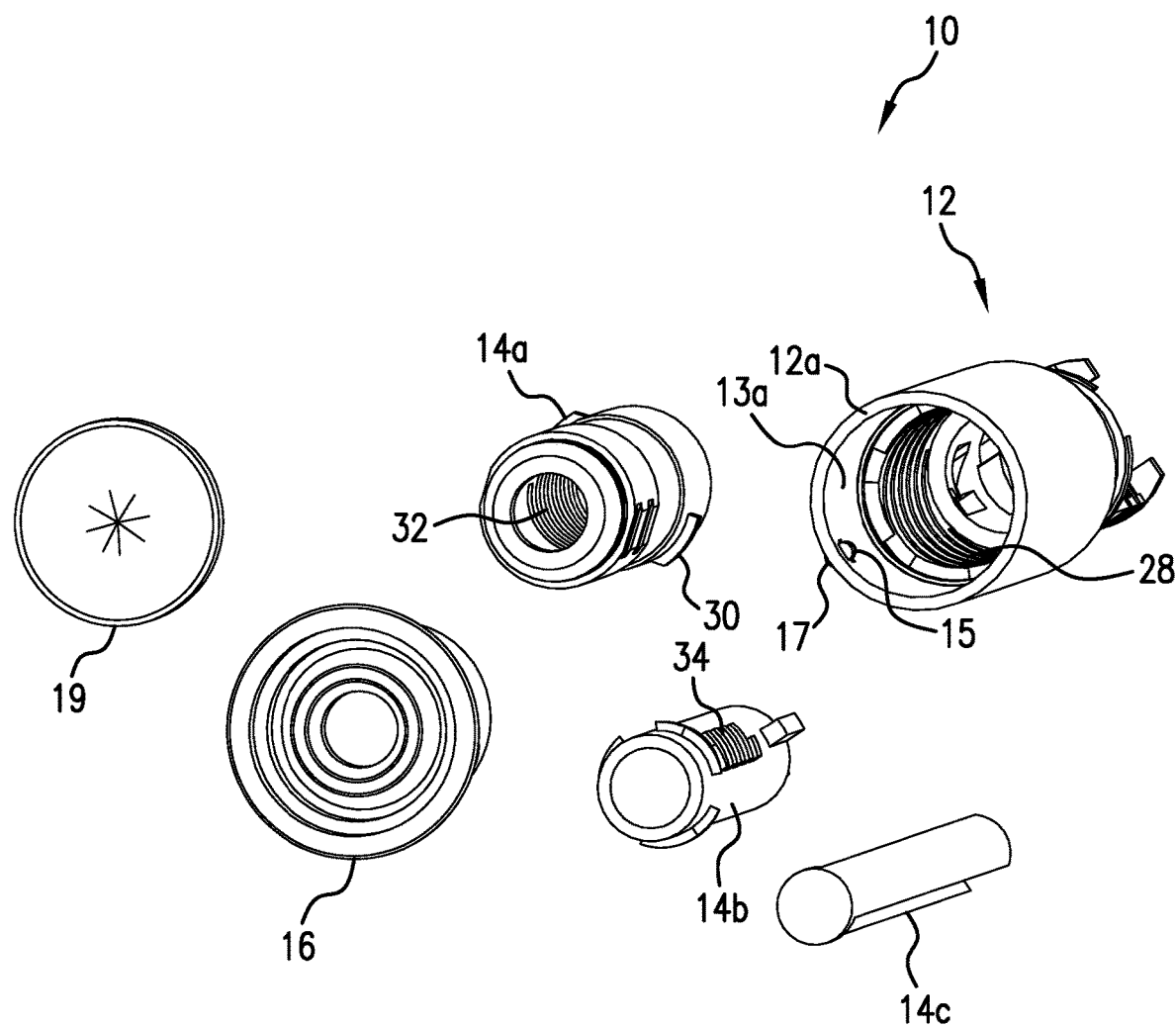
FIG. 4 is a partially exploded top perspective view of the injector shown in FIG. 1.
Figure 5:
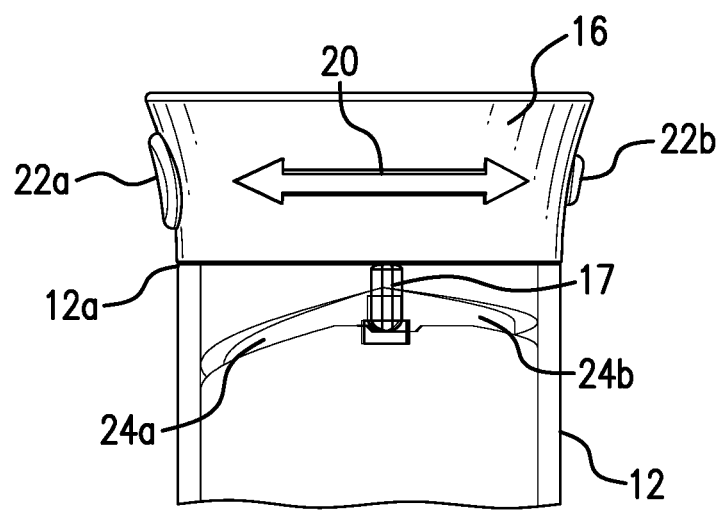
FIG. 5 is a magnified side elevation view of a portion of the injector shown in FIG. 1, wherein at least a portion of the injector (e.g., a body) is shown as transparent for clarity.

The injector 10 can include a plunger 14 disposed at least partially within the body 12 and movable with respect to the body 12 along the longitudinal axis L. As shown in FIGS. 3 and 4, the plunger 14 can include a threaded sleeve 14a, a threaded rod 14b, and/or a push rack 14c, which one of ordinary skill in the art would understand how these components cooperate to effectuate movement liquid and/or a needle for injection into a patient.

As shown in FIGS. 3 and 4, the interior surface 13a of the body 12 can include threads 28 sized, shaped and/or configured to engage threads or projections 30 on an exterior surface of the threaded sleeve 14a. Similarly, an interior surface of the threaded sleeve 14a can include threads 32 sized, shaped and/or configured to engage threads or projections 34 on an exterior surface of the threaded rod 14b.

However, the plunger 14 is not limited to any particular size, shape, configuration or even number of components. One of ordinary skill in the art would understand that various embodiments of the plunger 14 can be used to accomplish the functionality of injection described herein. For example, the plunger 14 can form, be attached to, and/or interact with a portion of a cartridge that contains the liquid, as described above. The cartridge can be removably attachable to the body 12.

During an injection, the piston or proximal seal of the cartridge moves toward the opposite end of the cartridge, thereby reducing the volume within the cartridge, and thus forcing a medication contained within the cartridge from the cartridge and through the needle. If, after injection, the piston were to be withdrawn back to its original position, the volume inside would be increased, thus drawing air or other foreign matter into the cartridge, and contaminating the contents of the cartridge. Accordingly, the piston should stay in position once an injection has been performed. In order for the device to be used for multiple injections, the end of the plunger in contact with the piston should also remain in contact with the piston to prevent a gap from forming between the plunger and the piston which would adversely affect the ability to deliver further metered doses. The opposite end of the plunger should also remain in contact with the actuator to prevent a similar gap from being formed between those components. In order to accomplish the above requirements, a directionally limited sliding arrangement may be provided between the actuator and the plunger. Such an arrangement provides that when the actuator is pulled outward to prepare for a dose being administered, the actuator is able to slide along the plunger without causing the plunger to be withdrawn or moved away from the piston, while when the actuator is pressed inward to deliver the dose, the plunger is fixed to the actuator such that movement of the actuator drives the plunger forward.

To accomplish this, and as understood by those skilled in the art, the injector 10 and/or plunger 14 can include one or more ratchets or escapement mechanisms. The one or more ratchets or escapement mechanisms (or other, functionally-equivalent mechanical features) permit movement of the actuator 16 in two opposite directions (e.g., toward and away from the injection site) along the longitudinal axis L, but permit movement of the plunger 14 in only one direction (e.g., toward the injection site) along the longitudinal axis L, while also precluding movement of the plunger 14 away from the piston. This allows the actuator 16 to be moved rearward until confirmation to set the predetermined dosage, while maintaining contact between at least a portion of the plunger 14 and the piston (e.g., rubber seal) of the cartridge. Without such structure or functionality, a gap would undesirably form between the plunger 14 and the cartridge, possibly resulting in no injection (when an injection is desired) or an incorrect or undesirable amount of liquid being injected into the patient. These features therefore allow the actuator 16 to be adjusted or moved to set a new dosage after each injection (in a step-wise fashion) without moving the plunger 14 with respect to the piston.

In particular, the first ratchet or escapement mechanism can maintain at least a portion of the plunger 14, such as the distal end of the push rack 14c or plunger 14, in contact with a proximal end of the piston (e.g., rubber seal) of the cartridge. However, the first ratchet or escapement mechanism may be omitted, and can be substituted with some other feature (e.g., a lip or other retention feature) to maintain the plunger 14 in contact with the piston of the cartridge. A second ratchet or escapement mechanism can maintain the threaded rod 14b in contact with the push rack 14c so that the plunger 14 is ready to effectuate an injection when the injector 10 is configured as intended.

The above structure allows at least a portion of the injector 10, such as the actuator 16, to be pulled proximally or away from the injection site, while another portion of the injector 10, such as the body 12 and/or the plunger 14, to be held in place. When the actuator 16 is pushed toward the injection site, the plunger 14 is caused to move forward with the actuator 16, thereby effectuating the injection. With each injection of the injector 10, the plunger 14 can move or advance the piston of the cartridge to force a predetermined volume of liquid through a double ended hypodermic needle, which can be attached to the injector 10 such that one end of the needle has pierced the closure of the cartridge. When the injector 10 and/or cartridge delivers the last dose of liquid from the cartridge, the injector 10 and/or the cartridge can be safely disposed.

The injector 10 can include the dose knob or actuator 16 positioned at the proximal end 12a of the body 12 and operably connected to the plunger 14. The actuator 16 can form or include a dose level selection mechanism or functionality, as described in detail below. The actuator 16 can be both rotatable with respect to the body 12 and linearly movable with respect to the body 12 along the longitudinal axis L. At least a portion of a lower or distal end of the actuator 16 can be positioned within and/or contact at least a portion of the interior surface 13a of the body 12 (see FIG. 3). At least a portion of the plunger 14, such as an upper or proximal end of the threaded sleeve 14a, can be positioned within and/or contact at least a portion of an interior surface of the actuator 16.

An exterior surface of the actuator 16 can include one or more indicators or displays to assist in the selection of a desired or appropriate dose. Each indicator may simply be indicia formed or printed on the actuator 16, or each indicator may be permanently or integrally formed on the actuator, such as a raised portion or a depressed portion. For example, as shown in FIGS. 1, 2 and 5-7, an arrow 20 can extend laterally on the actuator 16 to indicate that the actuator 16 can be rotated or twisted with respect to the body 12. A first symbol 22a can be located proximate to a left side of the arrow 20 to indicate a direction or position to achieve a higher dosing setting. A second symbol 22b can be located proximate to the right side of the arrow 20 to indicate a direction or position to achieve a lower dosing setting.

A spinner or push button 19 can be positioned adjacent to or within an upper or proximal end of the actuator 16. At least a lower or distal end of the spinner 19 can engage the upper or proximal end of the threaded sleeve 14a, thereby operably connecting the actuator 16 with the plunger 14. The spinner 19 may be a separate and distinct component from the actuator 16, or the spinner 19 can form a portion of the actuator 16 and integrally formed therewith.

As shown in FIGS. 1, 2 and 5-7, the actuator 16 can include a track 18. The track 18 can be configured to receive at least a portion of the track follower 15 therein. The track 18 can be in the form of a groove that extends inwardly into the actuator 16. The track 18 can have a generally rectilinear shape and include spaced-apart sidewalls. A distance between the sidewalls can be consistent throughout the track 18 and can be at least slightly greater than a diameter or width of the track follower 15, such that the track follower 15 can move within the track 18. As described in more detail below with respect to specific embodiments, the track 18 can include a first portion configured to limit travel of the actuator 16 along the longitudinal axis L to deliver a first predetermined amount of the liquid. The track 18 can also include a second portion configured to limit travel of the actuator 16 along the longitudinal axis L to deliver a second predetermined amount of the liquid.

Figure 6:
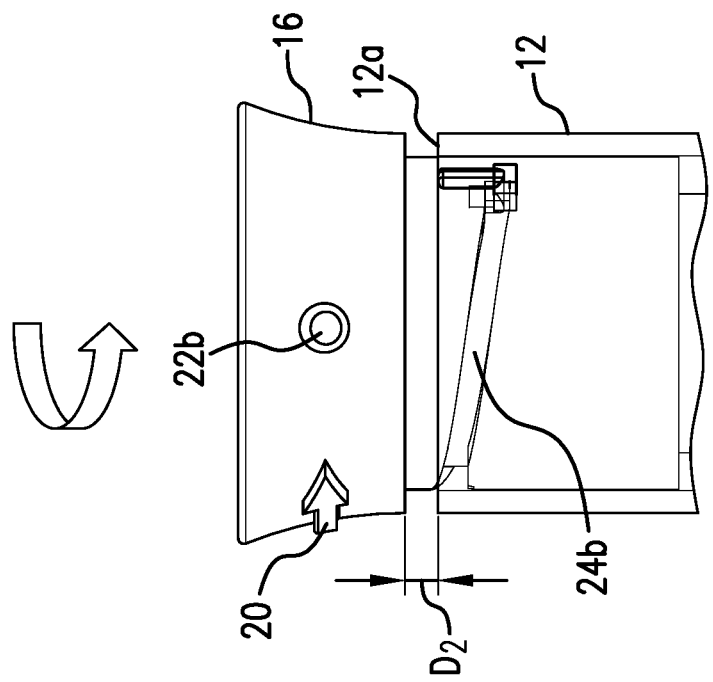
FIG. 6 is another magnified side elevation view of a portion of the injector shown in FIG. 1, wherein a track follower is position within one end of a track.
Figure 7:
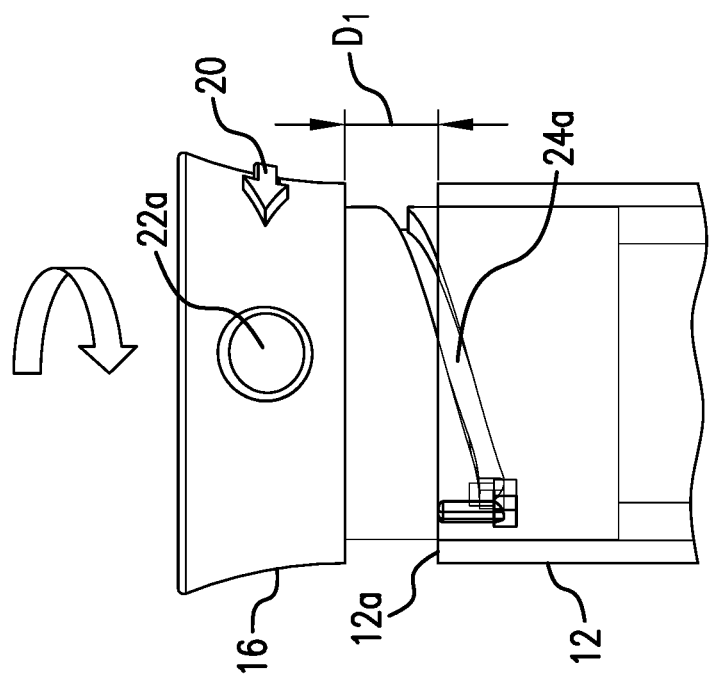
FIG. 7 is still a further magnified side elevation view of a portion of the injector shown in FIG. 1, wherein the track follower is positioned within an opposing end of the track.
Figure 9:
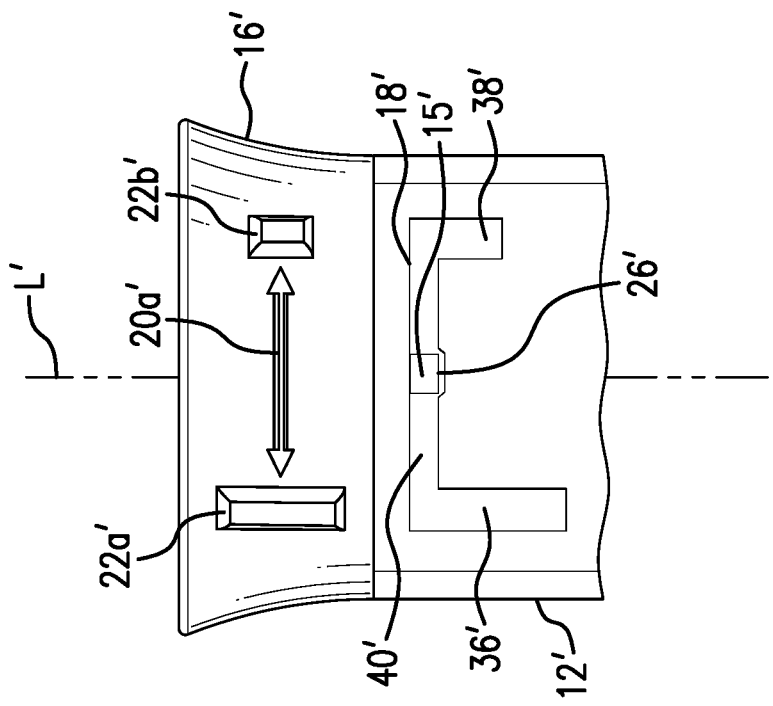
FIG. 9 is another magnified side elevation view of a portion of the injector shown in FIG. 8, wherein at least a portion of the injector (e.g., a body) is shown as transparent for clarity.
Figure 8:
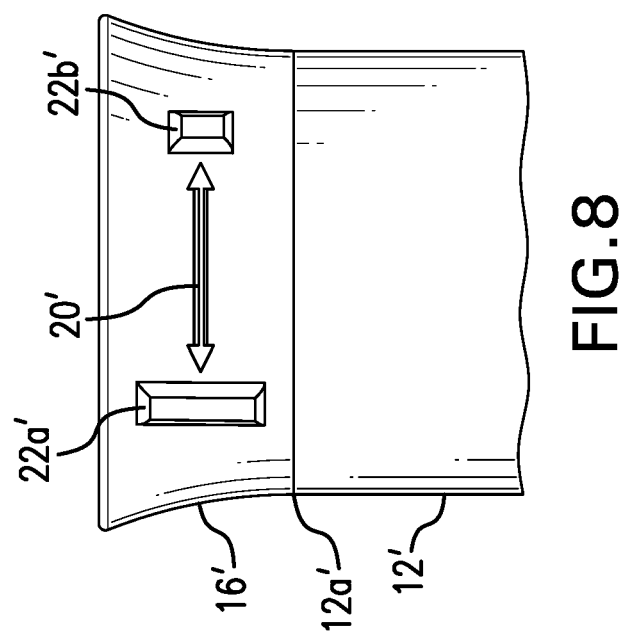
FIG. 8 is a magnified side elevation view of a portion of an injector according to an embodiment of the present disclosure.
Figure 12:
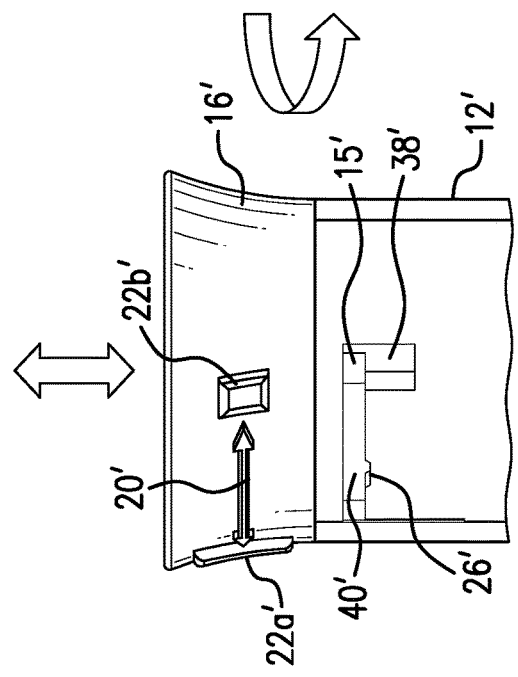
FIG. 12 is a magnified side elevation view of a portion of the injector shown in FIG. 9, wherein a track follower is positioned at a third location with respect to a track.
Figure 13:
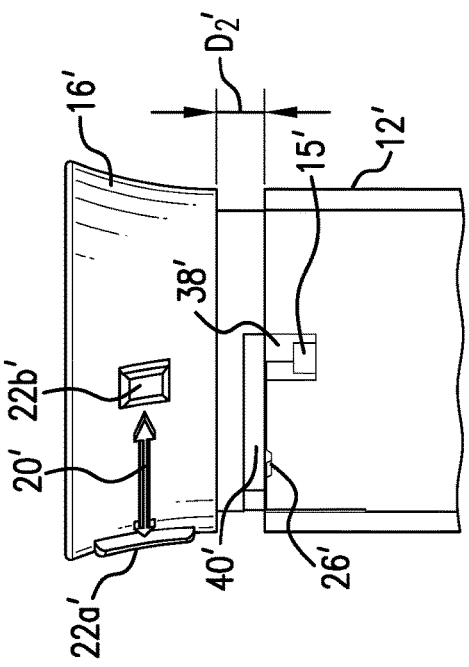
FIG. 13 is a magnified side elevation view of a portion of the injector shown in FIG. 9, wherein a track follower is positioned at a fourth location with respect to a track.
Figure 10:
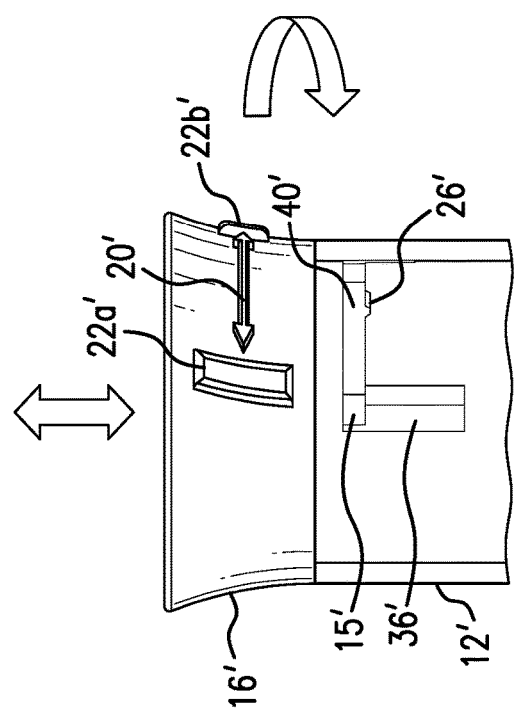
FIG. 10 is a magnified side elevation view of a portion of the injector shown in FIG. 9, wherein a track follower is positioned at a first location with respect to a track.
Figure 11:
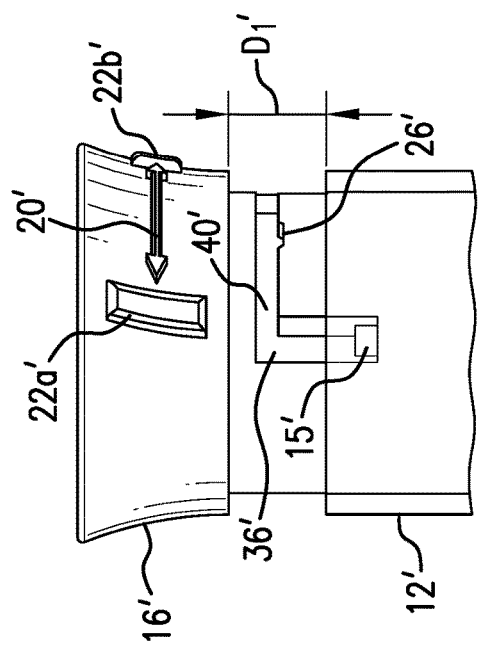
FIG. 11 is a magnified side elevation view of a portion of the injector shown in FIG. 9, wherein a track follower is positioned at a second location with respect to a track.

In operation, the actuator 16 can be positioned to selectively control displacement of the plunger 14 pursuant to the first portion or the second portion of the track 18. More particularly, in at least one embodiment, the actuator 16 can be rotated in a first direction (e.g., clockwise, as shown in FIGS. 6 and 10) to align the track follower 15 with the first portion of the track 18. The actuator 16 can also be rotated in a second direction (e.g., counterclockwise, as shown in FIGS. 7 and 12) to align the track follower 15 with the second portion of the track 18. In such embodiment, the first direction opposes the second direction.

The follower or cam dose level selection mechanism of the present disclosure can take one of many forms. Two representative embodiments are disclosed herein, each with a different feature set. These two different modes of operation may be preferable, one over the other, for different patient groups. However, the injector 10 and the dose level selection mechanism are not limited to only these two embodiments. There are a variety of designs which will allow a single fixed dose injector to become a multiple dose setting fixed dose injector, as will be apparent to those skilled in the art from the present disclosure.

Referring to FIGS. 1, 2 and 5-7, one embodiment of the dose level selection mechanism can be twisted to a first or a second dosage position, such as corresponding to a "high" or "low" dose position. The act of twisting to the selected dose position can raise the actuator 16 the length required by the selected dose. The actuator 16 can rest in this angular position. The user can then push the actuator 16 downward or inward toward the body 12 to deliver the dose. The act of delivering the dose can also return the actuator 16 to the neutral position. The dose volume can then be reselected for the next injection. Such an embodiment may be referred to as "Twist & Return".

The track 18 can extend around at least substantially an entire circumference of the actuator 16. The track 18 can extend at an angle of less than ninety degrees (90°) and greater than one degree (1°) with respect to the longitudinal axis L. The first portion of the track 18 can have a first end or stop (see FIG. 6), and the second portion of the track 18 can have an opposing second end or stop (see FIG. 7). The first end of the track 18 is spaced-apart from the second end of the track 18 along the longitudinal axis L. On one side of center or "neutral" (i.e., an apex), the track 18 can be in the form of a high-rise helix, and on the other side of center the track 18 can be in the form of a low-rise helix.

More particularly, in the present embodiment, the first portion of the track 18 can be a first angled or sloped section 24a and the second portion of the track 18 can be a second angled or sloped section 24b. The slope of the first angled section 24a can be greater than the slope of the second angled section 24b. The first and second angled sections 24a, 24b can meet or be joined at the apex of the track 18. The apex of the track 18 can include a notch 26 sized, shaped and/or configured to receive at least a portion of the track follower 15 therein.

Referring to FIG. 7, when the actuator 16 is turned or rotated in a first direction (e.g., left or counterclockwise), the track follower 15 can move or ride in the second sloped section 24b or the low-rise helix, causing the actuator 16 to be extended a shorter distance $D_2$. In other words, this rotation of the actuator 16 by the user causes the actuator 16 to move proximally or at least slightly away from the body 12. Following such movement, when the actuator 16 is depressed or moved linearly toward the body 12 in this configuration, the actuator 16 and associated mechanism move downward a corresponding short amount. This delivers a smaller dose of the liquid.

Conversely, when the actuator 16 is turned or rotated in a second direction (e.g., right or clockwise), the track follower 15 can move or ride in the first sloped section 24a or the high-rise helix, causing the actuator 16 to be extended a longer distance $D_1$ (see FIG. 6). In other words, this rotation of the actuator 16 by the user causes the actuator 16 to move proximally or at least slightly away from the body 12. Following such movement, when the actuator 16 is depressed or moved linearly toward the body 12 in this configuration, the actuator 16 and associated mechanism move downward a corresponding longer amount. This delivers a larger dose of the liquid.

In the present embodiment, the actuator 16 returns to the start position or the apex (or notch 26) of the track 18 after a dose is administered. The injector 10 does not return to the previous dose setting. Instead, the new higher or lower dose must be deliberately selected. For example, to administer a subsequent dose, the user must select the desired dose amount (i.e., high or low). This can be advantageous when the patient and doctor are titrating the dose. This feature is beneficial in assuring change of dose when change is preferred or required. Those of skill in the art will understand that the amount or volume of liquid delivered by the injector 10 in the "high" and "low" is not limited to a particular amount or volume, but may be any amount predetermined by a manufacturer or designer, for example.

FIGS. 8-12 show another embodiment of the injector 10', where like numerals are used to identify like elements and a prime symbol (') is used to distinguish like components of the injector 10' of the present embodiment from the injector 10 of the embodiment described above. The injectors 10, 10' of the two embodiments are substantially similar, and description of certain features that are identical or substantially similar between the embodiments may be omitted herein for the sake of brevity and convenience.

In this embodiment, the dose level selection mechanism can initially be moved, rotated or twisted (e.g., left/right or clockwise/counterclockwise) to select a fixed dose of higher or lower volume, and then pushed/pulled as with prior art single fixed dose injectors. Such an embodiment may be referred to as "Twist & Pull".

One unique feature of the present embodiment is that the first and second angled or sections 24a, 24b of the track 18, as described in detail above, are replaced by several linear portions. For example, the track 18' can include a first portion 36', a second portion 38', and a third portion 40'. The first portion 36' of the track 18' can extend parallel to the second portion 38' of the track 18'. The first portion 36' of the track 18' and the second portion 38' of the track 18' can extend parallel to the longitudinal axis L'. The first portion 36' of the track 18' can be longer than the second portion 38' of the track 18'. The third portion 40' of the track can extend between the first and second portions 36' and 38', respectively, of the track 18'. The third portion 40' of the track 18' can extend perpendicularly to the first and second portions 36', 38' of the track 18'.

In operation, when the actuator 16' is moved or twisted in a first direction (e.g., left or counterclockwise), the track follower 15' moves within the third portion 40' of the track 18' to an upper or proximal end of the second portion 38' of the track 18'. Such positioning allows for a relatively short stroke or movement of the actuator 16' and delivery of a smaller dose of the liquid in the injector 10' by pushing the actuator 16' toward the body 12'. When the actuator 16' is moved or twisted in a second direction (e.g., right or clockwise), the track follower 15' moves within the third portion 40' of the track 18' to an upper or proximal end of the first portion 36' of the track 18'. Such positioning allows for a relatively long stroke or movement of the actuator 16' and delivery of a larger dose by pushing the actuator 16' toward the body 12'.

In this embodiment, the actuator 16' will stay in the selected "high" dose or "low" dose position after the injection (i.e., push/pull) unless and until the actuator 16' is twisted or rotated. For example, a user can continue to inject liquid using the long stroke of the first portion 36' without being required to rotate the actuator 16'. This is a feature that can provide convenience to the user.

It is understood by those skilled in the art that the present embodiment is not limited to only two separate dosage amounts (i.e., high or low). The present embodiment may be modified to include three or more dosage amounts, such that the track 18' can include additional segments or portions (such as a fourth portion and a fifth portion) that are spaced-apart from the first and second portions 36', 38' and extend parallel thereto.

An advantage of the injectors 10, 10' over prior art injectors, which are used for products requiring a few discrete levels of dose titration due to a wider therapeutic window (relative to more continuous scales of dose titration such as those used for narrow therapeutic window biopharmaceuticals such as insulin, or growth hormone therapies), is that actively setting the correct dosage level for each injection event is eliminated. The injectors 10, 10' of the present disclosure maintain the ability to modify the dose setting in a single device, but reduce the potential user error of being required to carefully set the dose prior to each administration. Additionally, the injectors 10, 10' of the present disclosure eliminate the need for the user to manage inventory, storage, and/or procurement of separate devices for each titratable dose.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An injector for delivering liquid, the injector comprising:
a body having a proximal end, an opposing distal end, a longitudinal axis extending therebetween, and a track follower adjacent to the proximal end;
a plunger disposed at least partially within the body and movable with respect to the body along the longitudinal axis;
an actuator positioned at the proximal end of the body and operably connected to the plunger, the actuator comprising a track including a first portion and a second portion, the first portion limiting travel of the actuator along the longitudinal axis to deliver a first predetermined amount of the liquid, the second portion limiting travel of the actuator along the longitudinal axis to deliver a second predetermined amount of the liquid, the first predetermined amount being different than the second predetermined amount, the actuator being positionable to selectively control displacement of the plunger pursuant to the first portion or the second portion of the track; and
a directionally limited sliding arrangement between the actuator and the plunger, wherein when the actuator is pulled outward to prepare for a dose being administered, the actuator is able to slide along the plunger without causing the plunger to be withdrawn or moved away from a piston, while when the actuator is pressed inward to deliver the dose, the plunger is fixed to the actuator such that movement of the actuator drives the plunger forward,
wherein the track further comprises a third portion extending between the first and second portions, the third portion extending perpendicularly to the first and second portions.

2. The injector of claim 1, wherein the liquid is a medicament, and wherein the plunger forms a portion of a cartridge that contains the medicament, the cartridge being removably attachable to the body.

3. The injector of claim 1, wherein the body includes an interior surface and an opposing exterior surface, wherein the track follower comprises a projection that extends at least slightly inwardly from the interior surface of the body, and wherein the track is configured to receive at least a portion of the track follower therein.

4. The injector of claim 1, wherein the actuator is configured to be rotated in a first direction to align the track follower with the first portion of the track, and wherein the actuator is configured to be rotated in a second direction to align the track follower with the second portion of the track, the first direction being opposite to the second direction.

5. The injector of claim 1, wherein the first portion of the track extends parallel to the second portion of the track.

6. The injector of claim 1, wherein the first and second portions of the track extend parallel to the longitudinal axis.

7. The injector of claim 1, wherein the first portion is longer than the second portion.

8. The injector of claim 1, wherein the track includes a first sloped section and a second sloped section, and wherein an angle of the first sloped section is greater than an angle of the second sloped section.

9. The injector of claim 1, wherein the track includes a first sloped section and a second sloped section, and wherein the first sloped section intersects with the second sloped section at an apex of the track.

10. The injector of claim 1, wherein the apex of the track includes a notch configured to receive at least a portion of the track follower therein.

11. An injector for delivering medicament, the injector comprising:
a body having a proximal end, an opposing distal end, a longitudinal axis extending therebetween, and a track follower adjacent to the proximal end, track follower being a projection that extends at least slightly inwardly from an interior surface of the body;
a plunger disposed at least partially within the body and movable with respect to the body along the longitudinal axis;
an actuator positioned at the proximal end of the body and operably connected to the plunger, the actuator comprising a track configured to receive at least a portion of the track follower therein, the track comprising a first portion and a second portion, the first portion limiting travel of the actuator along the longitudinal axis to deliver a first predetermined amount of the medicament the second portion limiting travel of the actuator along the longitudinal axis to deliver a second predetermined amount of the medicament, the first predetermined amount being different than the second predetermined amount, the actuator being positionable to selectively control displacement of the plunger pursuant to the first portion or the second portion of the track; and
a directionally limited sliding arrangement between the actuator and the plunger, wherein when the actuator is pulled outward to prepare for a dose being administered, the actuator is able to slide along the plunger without causing the plunger to be withdrawn or moved away from a piston, while when the actuator is pressed inward to deliver the dose, the plunger is fixed to the actuator such that movement of the actuator drives the plunger forward,
wherein the track further comprises a third portion extending between the first and second portions, the third portion extending at least substantially perpendicularly to the first and second portions.

12. The injector of claim 11, wherein the actuator is configured to be rotatable in a first direction to align the track follower with the first portion of the track, and wherein the actuator is configured to be rotatable in a second direction to align the track follower with the second portion of the track, the first direction being opposite to the second direction.

13. The injector of claim 12, wherein the first and second portions of the track extend at least substantially parallel to the longitudinal axis, and wherein the first portion is longer than the second portion.

14. The injector of claim 12, wherein the track includes a first sloped portion in the form of a high-rise helix and a second sloped portion in the form of a low-rise helix, wherein the first and second sloped portions of the track intersect at an apex.

15. The injector of claim 14, wherein an angle of the first sloped portion is greater than an angle of the second sloped portion.

16. An injector for delivering liquid, the injector comprising:
a body having a proximal end, an opposing distal end, a longitudinal axis extending therebetween, and a track follower adjacent to the proximal end;
a plunger disposed at least partially within the body and movable with respect to the body along the longitudinal axis;
an actuator positioned at the proximal end of the body and operably connected to the plunger, the actuator comprising a track including a first portion, a second portion, and a third portion, the first portion being spaced-apart from the second portion, the first portion extending at least substantially parallel to the second portion and the longitudinal axis, the third portion extending at least substantially perpendicularly to the first portion, the first portion limiting travel of the actuator along the longitudinal axis to deliver a first predetermined amount of the liquid, the second portion limiting travel of the actuator along the longitudinal axis to deliver a second predetermined amount of the liquid, the first predetermined amount being different than the second predetermined amount, the actuator being positionable to selectively control displacement of the plunger pursuant to the first portion or the second portion of the track, the actuator being rotatable in a first direction to align the track follower with the first portion of the track, the actuator being rotatable in a second direction to align the track follower with the second portion of the track, the first direction being opposite to the second direction; and
a directionally limited sliding arrangement between the actuator and the plunger, wherein when the actuator is pulled outward to prepare for a dose being administered, the actuator is able to slide along the plunger without causing the plunger to be withdrawn or moved away from a piston, while when the actuator is pressed inward to deliver the dose, the plunger is fixed to the actuator such that movement of the actuator drives the plunger forward.

17. The injector of claim 16, wherein the liquid is a medicament, and wherein the plunger forms a portion of cartridge that contains the medicament, the cartridge being removably attachable to the body.

18. The injector of claim 16, wherein the body includes an interior surface and an opposing exterior surface, wherein the track follower is a projection that extends at least slightly inwardly from the interior surface of the body, and wherein the track is configured to receive at least a portion of the track follower therein.

* * * * *